United States Patent [19]

Okabe et al.

[11] 4,289,786
[45] Sep. 15, 1981

[54] FARNESYLACETIC ACID ESTER DERIVATIVES

[75] Inventors: Susumu Okabe, Kyoto; Yoshiaki Omura, Okayama; Yoichi Ninagawa; Yoshiji Fujita, both of Kurashiki, all of Japan

[73] Assignee: Kuraray Co., Ltd., Kurashiki, Japan

[21] Appl. No.: 96,570

[22] Filed: Nov. 21, 1979

[30] Foreign Application Priority Data

Nov. 28, 1978 [JP] Japan .................. 53-147622

[51] Int. Cl.³ .................. A61K 31/23; C09F 5/08
[52] U.S. Cl. .................. 424/312; 260/326.45; 260/404; 544/399; 546/248; 424/267; 424/274; 424/250
[58] Field of Search .................. 544/399; 260/404; 424/312

[56] References Cited

U.S. PATENT DOCUMENTS 3,154,570 10/1964 Adami et al. .................. 260/410.5
3,928,403 12/1975 Fujita et al. .................. 260/410.9 N
4,025,539 5/1977 Fujita et al. .................. 260/410.9 N

FOREIGN PATENT DOCUMENTS 1420802 1/1976 United Kingdom .

OTHER PUBLICATIONS

Crescenzi et al., "Il Farmaco, Ed., SC", vol. 19, (1964), pp. 757-764.
Minoli et al., "Il Farmaco", vol. 28, (1973), pp. 534-544.

Primary Examiner—Anton H. Sutto
Attorney, Agent, or Firm—Barry Kramer

[57] ABSTRACT

Novel farnesylacetic acid ester derivatives containing an amine nitrogen in the alcohol residue thereof and represented by the following general formula exhibit high levels of antiulcerogenic activity and very low levels of toxicity:

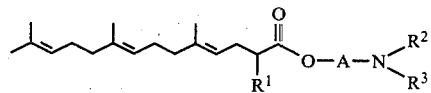

wherein A is an alkylene radical containing at least 2 carbon atoms; $R^1$ is H, alkyl, cycloalkyl, aryl, aralkyl or alkenyl; $R^2$ and $R^3$ are independently H, alkyl, aryl, aralkyl or alkenyl or one of $R^2$ and $R^3$ forms, together with A, a piperidine, pyrrolidine, tetrahydropyrimidine or piperazine ring which contains the nitrogen atom lying therebetween or $R^2$ and $R^3$ combine to form, together with the adjacent nitrogen atom, a piperazine ring; provided that the total number of carbon atoms contained in A, $R^1$, $R^2$ and $R^3$ is at least 5.

20 Claims, No Drawings

FARNESYLACETIC ACID ESTER DERIVATIVES

BACKGROUND OF THE INVENTION

1. Field of the Invention

This invention relates to novel farnesylacetic acid ester derivatives containing an amine nitrogen in the alcohol residue thereof and to the use thereof as antiulcer agents.

Farnesylacetic acid esters have heretofore been the object of a number of investigations because of their utility principally as medicinals, especially as antiulcer agents, and a number of methods for their preparation have been proposed (for example, U.S. Pat. Nos. 3,154,570; 3,928,403 and 4,025,539 and British Pat. No. 1,420,802). Typical of the farnesylacetic acid esters is the geraniol ester (3,7-dimethyl-2,6-octadienyl 5,9,13-trimethyl-4,8,12-tetradecatrienoate) which exhibits high antiulcerogenic activity and has found wide use in clinical medicine.

2. Description of the Prior Art

In most of the known farnesylacetic acid esters, the alcohol residue is, for example an alkanol residue or a terpene alcohol residue. The known farnesylacetic acid esters containing a nitrogen atom in their alcohol residue only include the following 5 compounds described in Il Farmaco, Ed. Sc., vol. XIX, fasc. 9, pp. 757–764 (1964):

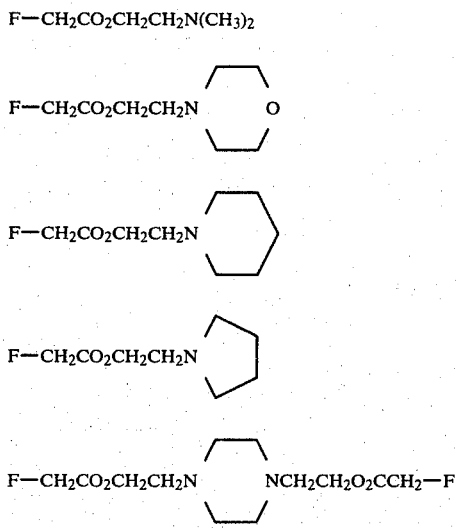

In the above formulas, F represents a farnesyl group. However, these compounds reportedly are inactive or only moderately active as far as antiulcer activity is concerned.

SUMMARY OF THE INVENTION

Contrary to the teachings of the prior art, it has now been found in accordance with the present invention that certain farnesylacetic acid esters containing an amine nitrogen in the alcohol residue with the number of carbon atoms contained in said residue being increased have a very high antiulcerogenic activity. Accordingly, the present invention provides novel farnesylacetic acid ester derivatives containing an amine nitrogen in the alcohol residue thereof and antiulcer agents containing said derivatives as active ingredients.

The farnesylacetic acid ester derivatives of the present invention are represented by the following general formula (I):

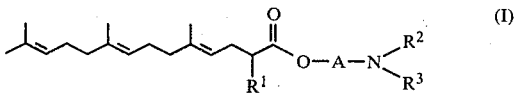

wherein A is a straight or branched alkylene radical containing 2 or more carbon atoms, $R^1$ is a hydrogen atom or an alkyl, cycloalkyl, aryl, aralkyl or alkenyl group, and $R^2$ and $R^3$ are the same or different and each can be a hydrogen atom or an alkyl, aryl, aralkyl or alkenyl group or either one of them is such that it forms, together with A, a piperidine, pyrrolidine, tetrahydropyrimidine or piperazine ring which contains as a constituent thereof the nitrogen atom lying therebetween, or $R^2$ and $R^3$ combine to form, together with the adjacent nitrogen atom, a piperazine ring, provided that the total number of carbon atoms contained in said A, $R^1$, $R^2$ and $R^3$ groups is at least five (5). The farnesylacetic acid ester derivatives include not only compounds of formula (I) but also pharmaceutically acceptable salts thereof. Accordingly, the term "farnesylacetic acid ester derivatives" as used hereinafter is intended to include those compounds of formula (I) which may be in the form of pharmaceutically acceptable salts. Such salts include those acid addition salts and quaternary ammonium salts that are generally formed by such amine-nitrogen-containing compounds and are suited for therapeutic purposes. Examples of the acid which can be used for the acid addition salt formation are hydrochloric, hydrobromic, sulfuric, nitric, phosphoric and other inorganic acids and citric, acetic, oxalic, fumaric, lactic, succinic, tartaric, methanesulfonic and other organic acids. Especially preferred is the hydrochloric acid salt.

DETAILED DESCRIPTION OF THE INVENTION

In the farnesylacetic acid ester derivatives represented by formula (I), the alkylene group represented by A is intended to denote a straight or branched divalent hydrocarbon group containing 2 or more but preferably not more than 10 carbon atoms in its principal chain, and, when A forms, together with $R^2$ or $R^3$, a five- or six-membered heterocycle which contains at least one nitrogen atom, the above-mentioned alkylene group is intended to denote a group in which one of its hydrogen atoms has been substituted by $R^2$ or $R^3$. It has been found that farnesylacetic acid ester derivatives in which A is an alkylene group containing only one carbon atom in its principal chain, such as $-CH_2-$ or $-CH(CH_3)-$, do not show any antiulcerogenic activity. More particularly, A in formula (I) may be represented by the following formula:

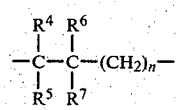

wherein $R^4$, $R^5$, $R^6$ and $R^7$ are the same or different and each is a hydrogen atom or a lower alkyl group having 1 to 5 carbon atoms, such as methyl, ethyl, propyl, isopropyl, butyl or pentyl, or any one of them forms, together with R² or R³, a piperidine, pyrrolidine, tetrahydropyrimidine or piperazine ring which contains as a constituent thereof the nitrogen atom to which R² and R³ are bonded, and n is an integer of 0 or 1.

The substituent R¹ which may be present in the alpha-position of the farnesylacetic acid ester derivative of formula (I) includes alkyl groups such as methyl, ethyl, propyl, isopropyl, butyl, pentyl, neopentyl, hexyl and octyl, cycloalkyl groups such as cyclopentyl and cyclohexyl, aryl groups such as phenyl, tolyl and naphthyl, aralkyl groups such as benzyl, phenylethyl and cinnamyl, and alkenyl groups such as vinyl, propenyl, butenyl, octenyl, prenyl, geranyl and farnesyl. Among these, preferred are lower alkyl groups having 1 to 5 carbon atoms, alkenyl groups having 3 to 10 carbon atoms, cyclohexyl, phenyl and benzyl. Not only can such substituted farnesylacetic acid ester derivatives be employed but also unsubstituted farnesylacetic acid ester derivatives wherein R¹ is a hydrogen atom have been found to be useful compounds within the scope of the present invention.

In formula (I), R² and R³ may independently be selected from the group consisting of a hydrogen atom and those alkyl, aryl and aralkyl groups described hereinabove in relation to R¹. Preferably, R² and R³ are selected from the group consisting of a hydrogen atom, lower alkyl groups having 1 to 5 carbon atoms, alkenyl groups having 3 to 15 carbon atoms, cyclohexyl, phenyl and benzyl. More preferably, in these cases, A is selected from the following alkylene groups: —CH₂CH₂—, —CH₂CH₂CH₂—, —CH(CH₃)—CH₂—, —CH₂—CH(CH₃)—, —C(CH₃)₂—CH₂—, —CH₂—C(CH₃)₂— and —C(CH₃)₂—CH₂CH₂—. Alternatively, one of R² and R³ can be one of the above-mentioned groups and the other may be a group which forms, together with A, a piperidine, pyrrolidine, tetrahydropyrimidine or piperazine ring which contains as a constituent the nitrogen atom lying therebetween. In such a case, A is preferably an alkylene group represented by the formula:

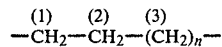

wherein n is an integer of 0 or 1, and more preferably, the carbon atom numbered (1), (2) or (3) is bonded to R² or R³ so as to form a piperidine or pyrrolidine ring together with the nitrogen atom to which R² and R³ are bonded, or the carbon atom (2) when n=0 or the carbon atom (3) when n=1 is bonded to R² or R³ so as to form a piperazine or tetrahydropyrimidine ring. Alternatively, R² and R³ may combine to form, together with the adjacent nitrogen atom, a piperazine ring. According to the present invention, a condition is imposed that the total number of carbon atoms, contained in A, R¹, R² and R³ should be at least 5 and preferably not more than 30 irrespective of the kinds of those groups. Such a restriction concerning the number of carbon atoms is related principally to the adaptability of the farnesylacetic acid ester derivatives as drugs, which exhibit antiulcer activity with essentially no associated toxicity.

Therefore, as will be understood from the above explanation, a preferred group of farnesylacetic acid ester derivatives of the present invention can be represented by the following general formula (I-1).

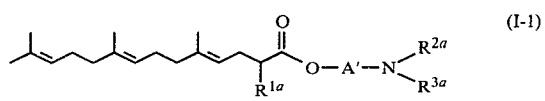

In formula (I-1), A' is a lower alkylene group represented by —CH₂CH₂—, —CH₂CH₂CH₂—, —CH(CH₃)—CH₂—, —CH₂—CH(CH₃)—, —C(CH₃)₂—CH₂—, —CH₂—C(CH₃)₂— or —C(CH₃)₂—CH₂CH₂—, R¹ᵃ is a hydrogen atom, a lower alkyl group having 1 to 5 carbon atoms, an alkenyl group having 3 to 10 carbon atoms, cyclohexyl, phenyl or benzyl, and R²ᵃ and R³ᵃ are the same or different and each can be a hydrogen atom, a lower alkyl group having 1 to 5 carbon atoms or an alkenyl group having 3 to 15 carbon atoms, provided that the total number of carbon atoms, contained in A', R¹ᵃ, R²ᵃ and R³ᵃ is 5 to 30. Those compounds of formula (I-1) not only show high levels of antiulcerogenic activity but also are generally significantly low in toxicity. These facts are quite advantageous in drugs to be used continuously over a relatively long period of time.

Another preferred group of farnesylacetic acid ester derivatives in accordance with the present invention can be represented by the following general formula (I-2).

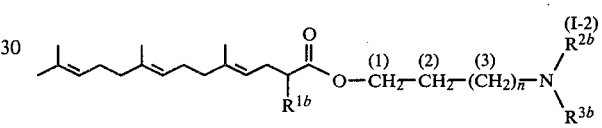

In formula (I-2), n is an integer of 0 or 1, R¹ᵇ is a hydrogen atom, a lower alkyl group having 1 to 5 carbon atoms, an alkenyl group having 3 to 10 carbon atoms, cyclohexyl, phenyl or benzyl, and R²ᵇ and R³ᵇ combined to form, together with the nitrogen atom to which R²ᵇ and R³ᵇ are bonded, a piperazine ring, or R³ᵇ independently represents a hydrogen atom, a lower alkyl group having 1 to 5 carbon atoms, an alkenyl group having 3 to 15 carbon atoms, phenyl or benzyl and R²ᵇ represents a group which, substituting a hydrogen atom on one of the carbon atoms numbered (1), (2) and (3), forms a piperidine or pyrrolidine ring together with the nitrogen atom to which R²ᵇ and R³ᵇ are bonded, or a group which, substituting one or two hydrogen atoms on the carbon atom numbered (2) when n is 0 or substituting one or two hydrogen atoms on the carbon atom numbered (3) when n is 1, forms a piperazine or tetrahydropyrimidine ring together with the nitrogen atom to which R²ᵇ and R³ᵇ are bonded, provided that the total number of carbon atoms contained in R¹ᵇ, R²ᵇ and R³ᵇ is 3 to 28, when n is 0, or 2 to 27 when n is 1. The piperazine ring which R²ᵇ and R³ᵇ combine to form together with the adjacent nitrogen atom in formula (I-2) may be represented by the formula

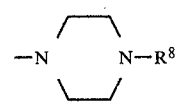

wherein R⁸ is a lower alkyl group having 1 to 5 carbon atoms, a hydroxyalkyl group having 1 to 5 carbon atoms, phenyl, benzyl or 3,4-methylenedioxybenzyl.

The following list provides examples of the farnesylacetic acid ester derivatives of the present invention. The compounds in the list other than quaternary ammonium salts include, within the meaning thereof, the hydrochlorides and hydrobromides. In the structural formulas, the symbols F—, G— and P— represent farnesyl

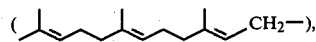

geranyl

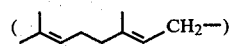

and prenyl

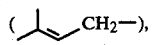

respectively.

| | |
|---|---|
| F—$CH_2CO_2CH_2CH_2N(C_2H_5)_2$ | (1) |
| F—$CH_2CO_2CH_2CH_2N^{\oplus}(C_2H_5)_3 \cdot Br^{\ominus}$ | (2) |
| F—$CH_2CO_2CH_2CH_2N(CH(CH_3)_2)_2$ | (3) |
| F—$CH_2CO_2CH_2CH_2CH_2N(CH_3)_2$ | (4) |
| F—$CH_2CO_2CH_2CH_2CH_2N^{\oplus}(CH_3)_3 \cdot Cl^{\ominus}$ | (5) |
| F—$CH_2CO_2CH_2CH_2CH_2N(C_2H_5)_2$ | (6) |
| F—$CH_2CO_2C(CH_3)_2CH_2N(CH_3)_2$ | (7) |
| F—$CH_2CO_2C(CH_3)_2CH_2N(C_2H_5)_2$ | (8) |
| F—$CH_2CO_2C(CH_3)_2CH_2N^{\oplus}(C_2H_5)_3 \cdot Br^{\ominus}$ | (9) |
| F—$CH_2CO_2CH_2C(CH_3)_2N(CH_3)_2$ | (10) |
| F—$CH_2CO_2CH(CH_3)CH_2N(C_2H_5)_2$ | (11) |
| F—$CH_2CO_2CH_2CH_2N(P)_2$ | (12) |
| F—$CH_2CO_2CH_2CH_2N(G)_2$ | (13) |

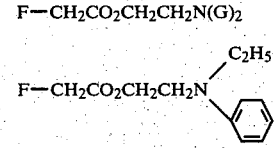 (14)

| | |
|---|---|
| F—$CH_2CO_2C(CH_3)_2CH_2CH_2N(CH_3)_2$ | (15) |

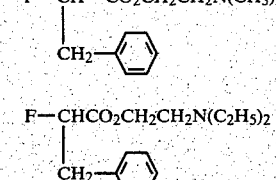 (16), (17), (18)

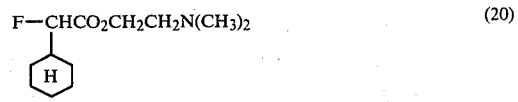 (19)

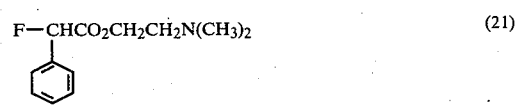 (20)

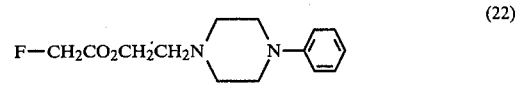 (21)

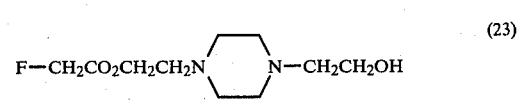 (22)

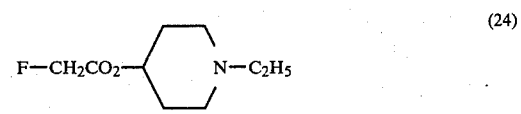 (23)

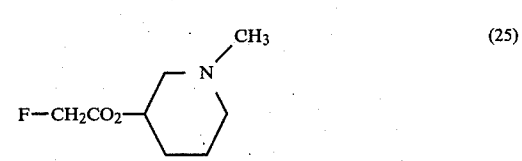 (24)

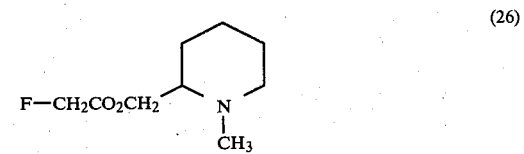 (25)

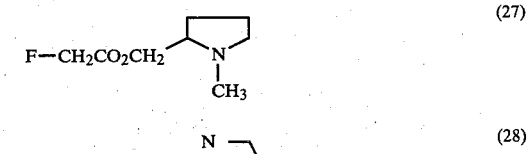 (26)

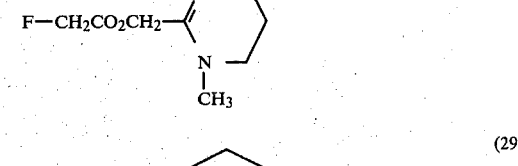 (27)

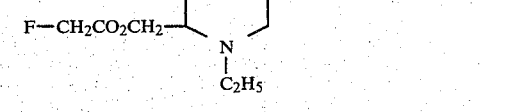 (28)

(29)

The pharmacological activity of the farnesylacetic acid ester derivatives of the present invention represented by formula (I) depends upon the nature of the substituents A, $R^1$, $R^2$ and $R^3$. Some compounds have higher antiulcer activity than other compounds, and vice versa. Some compounds may have very high preventive or curative effect against specific kinds of ulcers. Generally, however, it should be noted that the compounds of the present invention show, in every case, higher antiulcer activity than the geranyl ester of farnesylacetic acid which has been regarded as having the most excellent antiulcer activity. For some farnesylacetic acid ester derivatives of the present invention, there exist geometric isomers and/or optical isomers. The present invention also includes those isomers within the scope thereof.

The farnesylacetic acid ester derivatives of the present invention can be prepared by any of the conventional methods known for the preparation of known farnesylacetic acid esters except that the corresponding starting materials should be used. The most common method involves the reaction of a farnesylacetic acid or a functional derivative thereof represented by the formula (II)

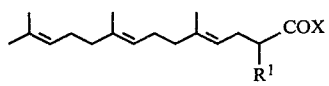

(II)

wherein $R^1$ is as defined in formula (I) and X is a group capable of forming esters on reaction with an alcoholic hydroxyl group, such as OH, halogen, OM (M being an alkali metal) or alkoxy, or a group capable of forming esters on reaction with a halide, such as OH or OM (M being an alkali metal), with an amine-nitrogen-containing compound represented by the formula (III)

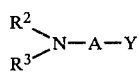

(III)

wherein A, $R^2$ and $R^3$ are as defined in formula (I) and Y is OH or a halogen atom, in the optional presence of an ester formation catalyst. The farnesylacetic acid or functional derivative thereof represented by formula (II) can easily be prepared, for example, by reacting nerolidol represented by formula (IV) with an orthoacetic acid ester represented by formula (V) in the presence of an acidic catalyst such as an organic, inorganic or Lewis acid, or by optionally subjecting the reaction product (VI) to ester exchange or alkaline hydrolysis or hydrolysis followed by halogenation using a halogenating agent such as thionyl chloride. The reactions involved are shown by the following scheme.

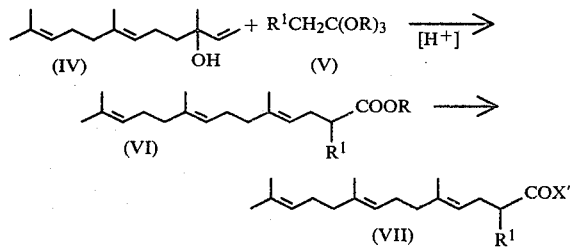

In formula (V), $R^1$ has the same meaning as in formula (I) and R is an alkyl of 1 to 8 carbon atoms. In formula (VII), X' has the same meaing as X has in formula (II) except that X' does not include OR.

The antiulcer agents which contain as active ingredient a farnesylacetic acid ester derivative represented by formula (I) or a pharmaceutically acceptable salt thereof in accordance with the present invention may take the form of tablets, capsules, powder, granules, lozenges, or liquid preparation as sterilized solution or suspension for oral or parenteral administration. Tablets, granules and powder are suitable dosage forms for orally administering the active ingredient of the present invention. Granules and powder may optionally take the form of capsules as unit dosage form. Solid preparations for oral administration may contain conventional pharmaceutically acceptable diluents (e.g. silicic anhydride, synthetic aluminosilicate, lactose, sugar, corn starch, microcrystalline cellulose), binders (e.g. gum arabic, gelatin, polyvinylpyrrolidone), lubricants (e.g. magnesium stearate, talc, silica), disintegrators (e.g. potato starch, carboxymethylcellulose calcium) and wetting agents (e.g. polyethylene glycol, sorbitan monooleate, sodium laurylsulfate). Tablets may be coated in a conventional manner. Liquid preparations for oral administration may be in the form of aqueous or oleaginous suspensions, solutions, syrups or the like, or they may be dried preparations to be dissolved or dispersed in appropriate vehicles prior to use. Such liquid preparations may contain emulsifiers (e.g. lecithin, sorbitan monooleate), auxiliaries for emulsifiers (e.g. sorbitol syrup, methylcellulose, gelatin), nonaqueous vehicles (e.g. coconut oil, peanut oil), antioxidants, coloring agents, flavoring substances, and the like that are conventional in the art. Liquid preparations for parenteral administration may be prepared by dissolving or suspending the farnesylacetic acid ester derivative of formula (I) in a sterile vehicle. Solutions are prepared by dissolving the active compound in a vehicle for injection, filtering and sterilizing the solution and filling ampules with the sterile solution followed by sealing hermetically. It is preferable, in this case, to add such auxiliaries as local anesthetic, preservative and buffer to the vehicle. Suspensions may be prepared substantially in the same manner as in the preparation of solutions except that the active compound is not dissolved but suspended in a vehicle and some other sterilizing procedure than filtration is used.

The pharmaceutical compositions of the present invention which contains the farnesylacetic acid ester derivative of formula (I) are effective for the treatment and/or prophylaxis of ulcers of the mammalian digestive tract, especially the gastric ulcer. The effective amount or dose of said compound depends on the severity of the ulcer, physical constitution of the patient, the specific compound of formula (I) employed and other factors. Generally, however, the daily dose for human adults is in the range of about 100 mg to about 2,500 mg.

The synthesis and pharmacological properties of specific farnesylacetic acid ester derivatives of the present invention are described in the following examples. Unless otherwise stated, all percentages and parts are by weight.

PREPARATION OF FARNESYLACETIC ACID ESTER DERIVATIVES

Example 1

A three-necked flask equipped with thermometer, dropping funnel and Vigreux column was charged with 41.7 g of methyl farnesylacetate, 32.0 g of 2-diethylaminoethanol, 1.0 g of potassium hydroxide and 200 ml of toluene. The contents were heated at a temperature of 110°–116° C. for 18 hours, while the methanol resulting from the reaction was removed with the toluene. During the reaction, toluene was dropped through the dropping funnel at a rate so as to compensate for the amount of toluene distilled off. After completion of the reaction, 200 ml of water and 200 ml of ether were added, and, after phase separation, the ether layer was washed with two 200-ml portions of water and then dried over anhydrous magnesium sulfate. The ether and toluene were distilled off from the ether layer. Subsequent vacuum distillation gave 30.0 g of a fraction boiling at 195° C. under 1.0 mmHg. Gas chromatographic analysis revealed that the fraction had a purity of 99% and proton NMR and mass spectrometry (hereinafter MS) identified it as 2-diethylaminoethyl farnesylacetate. The NMR data are shown below.

NMR (δ in CDCl₃ 60MHz)

| | | | |
|---|---|---|---|
| 0.95 | (t) | 6H | —N(CH₃/CH₃) |
| 1.40–1.65 | (m) | 12H | CH₃\〉= |
| 1.85–2.10 | (m) | 8H | \CH₂—CH₂/ |
| 2.15–2.30 | (m) | 4H | \CH₂—CH₂—CO— |
| 2.30–2.75 | (m) | 6H | —CH₂—N(CH₂—/CH₂—) |
| 4.10 | (t) | 2H | O‖—C—O—CH₂— |
| 4.80–5.25 | (m) | 3H | =CH |

(Broad peaks which were apparently singlets or doublets were all regarded as (m).)

To 27.30 g of diethylaminoethyl farnesylacetate prepared in this manner was added 210 g of water, followed by dropwise addition of 74.85 ml of 1 N hydrochloric acid, to prepare an aqueous solution of the hydrochloride. The solution was colorless and transparent and foamed on agitation.

Examples 2–9

Using the lower alkyl esters of farnesylacetic acids shown in Table 1 and the amino alcohols also shown in Table 1, ester exchange reaction was carried out by the procedure of Example 1, to prepare a variety of amine-nitrogen-containing farnesylacetic acid esters and hydrochlorides thereof. The results are summarized in Table 1. In the chemical formula appearing in the table, P stands for a prenyl group, G a geranyl group and F a farnesyl group.

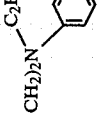

The NMR data for the compounds prepared in the above Examples 2-9 were as follows:

For Example 2: (δ in CDCl₃, ppm. 60 MHz); 1.40–1.80 (m. 14H), 1.85–2.10 (m. 8H), 2.14 (S. 6H), 2.15–2.30 (m. 4H), 4.08 (t. 2H), 4.80–5.25 (m. 3H).

For Example 3: (δ in CDCl₃, ppm. 90 MHz); 1.48–1.70 (m. 24H), 1.85–2.05 (m. 8H), 2.15–2.25 (m. 4H), 2.50 (5. 2H), 2.95 (d. 4H), 3.99 (t. 2H), 4.90–5.25 (m. 5H).

For Example 4: (δ in CDCl₃, ppm. 60 MHz); 1.50–1.70 (m. 30H), 1.88–2.10 (m. 16H), 2.14–2.30 (m. 4H), 2.56 (t. 2H), 3.02 (d. 4H), 4.03 (5. 2H), 4.85–5.35 (m. 7H).

For Example 5: (δ in CDCl₃, ppm. 90 MHz); 1.48–1.65 (m. 12H), 1.86–2.05 (m. 8H), 2.18–2.30 (m. 4H), 2.44 (t. 2H), 2.49 (S. 8H), 2.55 (t. 2H), 3.05 (s. 1H), 3.54 (t. 2H), 4.13 (t. 2H), 4.90–5.16 (m. 3H).

For Example 6: (δ in CCl₄, ppm. 60 MHz); 1.50–1.70 (m. 12H), 1.85–2.10 (m. 8H), 2.15–2.30 (m. 4H), 2.40–2.65 (m. 6H), 2.95–3.18 (m. 4H), 4.10 (t. 2H), 4.80–5.30 (m. 3H), 6.60–7.25 (m. 5H).

For Example 7: (δ in CDCl₃, ppm. 60 MHz); 1.10 (t. 3H), 1.47–1.70 (m. 12H), 1.85–2.10 (m. 8H), 2.15–2.35 (m. 4H), 3.20–3.65 (m. 4H), 4.85–5.30 (m. 3H), 6.60–7.25 (m. 5H).

For Example 8: (δ in CDCl₃, ppm. 60 MHz); 1.45–1.70 (m. 12H), 1.80–2.10 (m. 8H), 2.12 (s. 6H), 2.10–2.30 (m. 3H), 2.35 (t. 2H), 2.65–2.80 (m. 2H), 4.02 (t. 2H), 4.80–5.30 (m. 3H), 7.16 (s. 5H).

For Example 9: (δ in CDCl₃, ppm. 60 MHz); 0.98 (s. 6H), 1.45–1.65 (m. 12H), 1.85–2.10 (m. 8H), 2.20 (s. 6H), 2.15–2.35 (m. 4H), 3.93 (s. 2H), 4.80–5.20 (m. 3H).

Example 10

2-Methyl-2-dimethylaminopropyl farnesylacetate

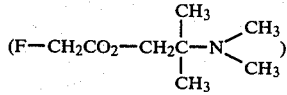

(30 g) prepared in Example 9 was placed in a 100-ml three-necked flask equipped with a thermometer and a reflux condenser and heated in a nitrogen atmosphere at 200° C. for 3 hours. After completion of the reaction, the reaction mixture was subjected to separation by silica gel column chromatography, which gave 15 g of 1,1-dimethyl-2-dimethylaminoethyl farnesylacetate

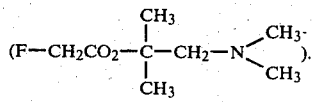

Proton NMR and MS served for identification. The proton NMR data are shown below.

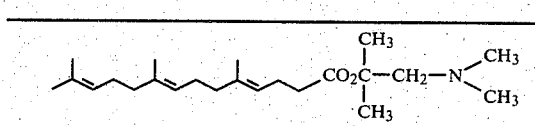

NMR (δ in CCl₄. 90 MHz)

| | | | |
|---|---|---|---|
| 1.37 | (s) | 6H | $-CO_2-\underset{CH_3}{\underset{|}{\overset{CH_3}{\overset{|}{C}}}}-$ |
| 1.50–1.65 | (m) | 12H | $\overset{CH_3}{\underset{}{\rangle}}=$ |
| 1.85–2.05 | (m) | 8H | $\diagdown CH_2-CH_2\diagup$ |
| 2.05–2.20 | (m) | 4H | $\diagdown CH_2-CH_2\diagdown_{CO_2-}$ |
| 2.26 | (s) | 6H | $-\underset{CH_3}{\overset{CH_3}{N\diagdown}}$ |
| 2.48 | (s) | 2H | $-\underset{|}{\overset{|}{C}}-CH_2-N\diagup$ |
| 4.90–5.15 | (m) | 3H | $=CH\diagup$ |

Example 11

In a 200-ml three-necked flask equipped with dropping funnel, thermometer and reflux condenser, there were placed 4.80 g of N-ethyl-4-hydroxypiperidine, 3.23 g of pyridine and 50 ml of benzene, and 11.60 g of farnesylacetyl chloride was added dropwise under reflux. After completion of the dropping, the mixture was refluxed for a subsequent 2 hour period and then cooled. Addition of 30 ml of 20% aqueous solution of sodium hydroxide, stirring, phase separation and silica gel column chromatography of the upper layer yielded 2.4 g of N-ethyl-4-farnesylacetoxy-piperidine as a pale-yellow liquid. The product was identified by proton NMR and mass spectrometry. The proton NMR data are shown in the following.

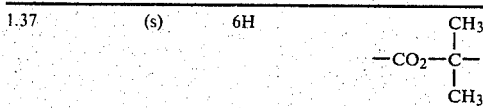

NMR (δ in CDCl₃ 90 MHz)

| | | | |
|---|---|---|---|
| 1.02 | (t) | 3H | $\diagdown N\diagdown_{CH_2CH_3}$ |
| 1.50–1.65 | (m) | 12H | $\overset{CH_3}{\underset{}{\rangle}}=$ |
| 1.65–1.85 | (m) | 4H | $\overset{CH_2}{\diagup}\diagdown N-$ |
| 1.85–2.05 | (m) | 8H | $\diagdown CH_2-CH_2\diagup$ |
| 2.15–2.35 | (m) | 6H | $\diagdown CH_2-CH_2\diagdown_{CO_2-}$ and $\underset{CH_2}{\overset{CH_2}{\langle}}N-CH_2-$ |
| 2.40–2.75 | (m) | 4H | $\underset{CH_2}{\overset{CH_2}{\langle}}N\diagdown$ |
| 4.56–4.90 | (m) | 1H | $-CO_2-CH\diagdown N-$ |

-continued

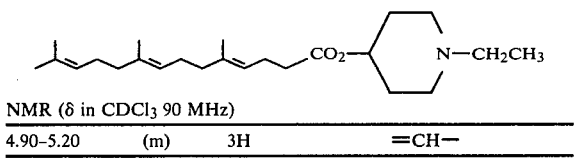

NMR (δ in CDCl₃ 90 MHz)

| 4.90–5.20 | (m) | 3H | =CH— |

To 2.2 g of this compound were added 6 ml of 1 N hydrochloric acid and water in an amount sufficient to make the total weight 24 g. Thus was obtained a 10% aqueous solution of N-ethyl-4-farnesylacetoxypiperidine hydrochloride. The aqueous solution was yellowish and transparent and foamed on agitation.

Examples 12 and 13

Using the procedure of Example 11, the amino alcohols shown in Table 2 and farnesylacetyl chloride were allowed to react to prepare the corresponding amine-nitrogen-containing farnesylacetic acid esters and aqueous solutions of the hydrochlorides. The results are summarized in Table 2.

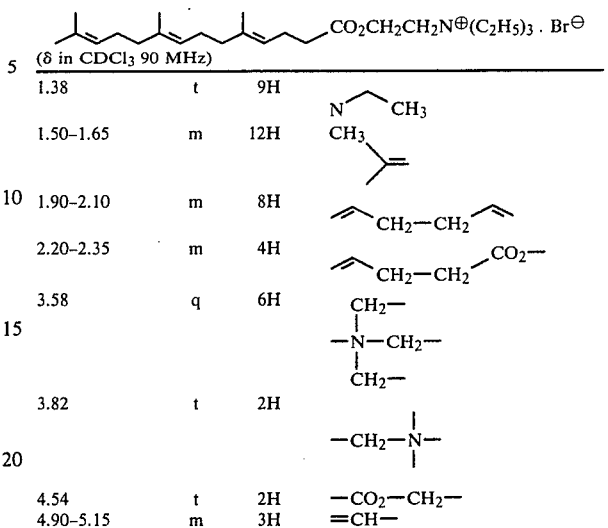

(δ in CDCl₃ 90 MHz)

| 1.38 | t | 9H | N–CH₃, CH₃ |
| 1.50–1.65 | m | 12H | |
| 1.90–2.10 | m | 8H | CH₂—CH₂ |
| 2.20–2.35 | m | 4H | CH₂—CH₂—CO₂— |
| 3.58 | q | 6H | CH₂—, —N—CH₂—, CH₂— |
| 3.82 | t | 2H | —CH₂—N— |
| 4.54 | t | 2H | —CO₂—CH₂— |
| 4.90–5.15 | m | 3H | =CH— |

TABLE 2

| | Starting materials | | Product | | | | Appearance of aqueous solution of hydrochloride |
|---|---|---|---|---|---|---|---|
| Example | Acid chloride (g) | Amino-alcohol (g) | Structural formula (g) | Appearance | Purified by | Identified by | |
| 12 | F—CH₂COCl (14.2) | HO—[N—CH₃ piperidine] (5.75) | F—CH₂CO₂—[N—CH₃ piperidine] (6.4) | Yellow liquid | Vacuum distillation 196–200° C. | Proton NMR and MS | Yellowish and transparant (10%) |
| 13 | F—CH₂COCl (15.6) | HOCH₂—[piperidine N—CH₃] (5.75) | F—CH₂CO₂CH₂—[piperidine N—CH₃] (7.1) | Yellow liquid | Vacuum distillation 196–200° C. | Proton NMR and MS | Yellowish and transparant (10%) |

NMR data

For Example 12: (δ in CDCl₃, ppm. 90 MHz)
1.25–1.90 (m. 16H), 1.90–2.16 (m. 8H), 2.27 (s. 3H), 2.17–2.45 (m. 6H),
2.50–2.77 (m. 2H), 4.73–4.95 (m. 1H), 4.95–5.25 (m. 3H)

For Example 13: (δ in CDCl₃, ppm. 90 MHz)
1.15–1.80 (m. 18H), 1.85–2.10 (m. 8H), 2.15–2.30 (m. 6H), 2.27 (s. 3H),
2.70–2.96 (m. 1H), 4.09 (d. 2H), 4.90–5.20 (m. 3H)

Example 14

2-Diethylaminoethyl farnesylacetate (10.9 g) prepared by the procedure of Example 1, 10 g of ethyl bromide and 50 ml of acetonitrile were placed in a three-necked flask equipped with a thermometer and a reflux condenser, and the reaction was allowed to proceed under reflux for 20 hours. Thereafter, the acetonitrile and unreacted ethyl bromide were distilled off and the solid residue was washed with petroleum ether and dried to give 11 g of a pale-yellow paste-like substance, which gave one single spot on a thin layer chromatogram (developing solvent: ethanol) and identified as farnesylacetoxyethyltriethylammonium bromide by proton NMR and elemental analysis. The proton NMR data were as shown below.

Example 15

3-Dimethylaminopropyl farnesylacetate (9.3 g) prepared by the procedure of Example 2 and 100 ml of acetonitrile were placed in a 200-ml three-necked flask equipped with thermometer, reflux condenser and gas inlet tube, and, while blowing methyl chloride into the flask contents, the reaction was allowed to proceed under reflux for 16 hours. Thereafter, most of the acetonitrile was distilled off and the remaining viscous liquid was subjected to silica gel column chromatography to give 7.2 g of a pale-yellow paste-like substance. Proton NMR and elemental analysis identified this substance as 3-farnesylacetoxytrimethylammonium chloride. Thin layer chromatography using ethanol as developing solvent gave only one spot. The proton NMR data were as shown below.

$$\text{[structure]} \quad CO_2CH_2CH_2CH_2N^{\oplus}(CH_3)_3 \cdot Cl^{\ominus}$$

NMR (δ in CDCl$_3$, ppm. 90 MHz)

| | | | |
|---|---|---|---|
| 1.50–1.65 | m | 12H | CH$_3$—C= |
| 1.85–2.10 | m | 8H | =CH—CH$_2$—CH$_2$—C= |
| About 2.15 | m | 2H | —CO$_2$—CH$_2$—CH$_2$—CH$_2$—N— |
| 2.20–2.30 | m | 4H | —CH$_2$—CH$_2$—CO$_2$— |
| 3.40 | s | 9H | —N(CH$_3$)$_3$ |
| About 3.80 | m | 2H | —CH$_2$—N— |
| 4.14 | t | 2H | —CO$_2$—CH$_2$— |
| 4.90–5.20 | m | 3H | =CH— |

PHARMACOLOGICAL ACTIONS

Antiulcerogenic activity

Example 16

Indomethacin-induced ulcer

After fasting for 24 hours, male Donryu rats weighing 210 to 230 grams were administered subcutaneously with indomethacin suspended in 1% aqueous solution of carboxymethylcellulose at a dosage level of 15 mg/kg. Seven hours later, the animals were sacrificed by ether inhalation. The rat stomach was cut open and the indomethacin-induced ulcers appearing on the gastric mucosa were measured for their length in mm. The total length of ulcers per animal was designated as the ulcer index. The farnesylacetic acid ester derivatives (test compounds) prepared by any of the synthetic procedures described above and geranyl farnesylacetate as a control were orally administered 10 minutes prior to the indomethacin administration. The antiulcerogenic activity was evaluated in terms of the prevention ratio, i.e. the quotient of the difference in ulcer index between the test compound group and the control group divided by the ulcer index for the control group. The results are shown in Table 3. The numbers in the test compound column are those previously assigned to the exemplary compounds of the present invention each represented by a structural formula, and the example numbers are the numbers of examples wherein preparation of the corresponding compounds is described. The test compounds were all hydrochlorides except for one quaternary ammonium salt.

TABLE 3

| Test compound No. | Example No. | Dose (mg/kg) | Number of animals | Prevention ratio (%) |
|---|---|---|---|---|
| Control | | 0 | 20 | — |
| (14) | 7 | 300 | " | 70.2 |
| (4) | 2 | " | " | 65.8 |
| (1) | 1 | " | " | 64.1 |
| (16) | 8 | " | " | 84.5 |
| (26) | 13 | " | 10 | 47.9 |
| (24) | 11 | " | " | 76.6 |
| (23) | 5 | " | " | 93.2 |
| (7) | 10 | " | " | 91.7 |
| (2) | 14 | " | " | 68.8 |
| (13) | 4 | " | " | 81.3 |

TABLE 3-continued

| Test compound No. | Example No. | Dose (mg/kg) | Number of animals | Prevention ratio (%) |
|---|---|---|---|---|
| Geranyl farnesyl-acetate | " | | 20 | 6.1 |

Example 17

Stress ulcer

Male Donryu rats weighing 240–260 grams were immobilized in wire cages (cf. Japanese Journal of Pharmacology, 18, 9–18 (1968)) and placed under stress by immersing them in water at 23° C. to the level of the breast. Seven hours later, the animals were taken up from the water tank and immediately sacrificed by blowing and the stomach was excised. The stomach was inflated with 1% formalin and then cut open and the ulcer on the gastric gland were measured for length in mm. The total ulcer length per animal was designated as the ulcer index. In the above-mentioned test, the compounds (hydrochlorides) (test compounds (1) and (4)) prepared by the procedure of Examples 1 and 2, respectively and geranyl farnesylacetate were administered orally to the rats 10 minutes before the immersion. The results are shown in Table 4. In the Table, the prevention ratio has the same meaning as defined for the indomethacin-induced ulcer in Example 16.

TABLE 4

| Test compound | Dose (mg/kg) | Number of animals | Prevention ratio (%) |
|---|---|---|---|
| Control | 0 | 30 | — |
| (1) | 300 | 20 | 42.1 |
| (4) | " | 20 | 40.1 |
| Geranyl farnesyl-acetate | " | 15 | 32.0 |

Acute toxicity—1

Wistar rats, five weeks of age, were fed previously for one week and then subjected to the test. All the test compounds were administered orally. The observation period was 2 weeks. The test compounds (4), (1) and (16) used were the products prepared in the above Examples 2, 1 and 8, respectively, and were all in the form of hydrochlorides. The results are shown in Table 5.

Acute toxicity—2

Five-week-old ddY mice were fed previously for one week and then subjected to the test. All the test compounds were administered orally and the observation period was one week. The test compounds (23), (7) and (13) used were the products of the above Example 5, 10 and 4, respectively and were all in the form of hydrochlorides (the product of Example 10 was converted into the hydrochloride by a conventional method). The results are shown in Table 6.

TABLE 5

| Test compound | Dose (g/Kg) | Number of dead animals/number of animals used | LD$_{50}$ (g/kg) |
|---|---|---|---|
| (4) | 3 | 0/5 | >4.0 |
| | 4 | 0/5 | |
| (1) | 4.1 | 0/5 | >5.4 |
| | 5.4 | 0/5 | |
| (16) | 5 | 0/5 | >15.0 |
| | 10 | 1/5 | |

TABLE 5-continued

| Test compound | Dose (g/Kg) | Number of dead animals/number of animals used | LD$_{50}$ (g/kg) |
|---|---|---|---|
| | 15 | 1/5 | |

TABLE 6

| Test compound | Dose (g/kg) | Number of dead animals/number of animals used | LD$_{50}$ (g/kg) |
|---|---|---|---|
| (23) | 1.3 | 0/3 | |
| | 4.0 | 2/4 | 4.0 |
| | 6.6 | 3/3 | |
| (7) | 6 | 0/4 | |
| | 8 | 1/3 | 8.4 |
| | 10 | 3/3 | |
| (13) | 1 | 0/3 | |
| | 2 | 1/3 | |
| | 6 | 2/3 | 7.0 |
| | 10 | 2/3 | |
| | 20 | 3/3 | |

The above results clearly show that the farnesylacetic acid ester derivatives of the present invention are very significantly low in toxicity. This will be more easily understood when compared with the fact that certain amino alcohol esters used as anticholinergic agents have LD$_{50}$ values of several scores to several hundred milligrams per kilogram of body weight. The LD$_{50}$ values in rats and mice for geranyl farnesylacetate are more than 8 g/kg.

Example 18

Dosage form suited for oral administration

The ingredients shown below were mixed and the resulting mixture was formed into tablets using a tableting machine.

| Ingredient | Weight (mg) per tablet |
|---|---|
| F—CH$_2$CO$_2$(CH$_2$)$_2$N(C$_2$H$_5$)$_2$ . HCl | 100 |
| Corn starch | 50 |
| Crystalline cellulose | 100 |
| Carboxymethylcellulose | 50 |
| Total | 300 |

Example 19

Capsules for oral administration

The following ingredients were mixed by a conventional method and the resulting mixture was packed in hard gelatin capsules.

| Ingredient | Weight (mg) per capsule |
|---|---|
| F—CH$_2$CO$_2$(CH$_2$)$_2$N(C$_2$H$_5$)$_2$ . HCl | 50 |
| Magnesium metasilicate aluminate | 150 |
| Corn starch | 100 |
| Total | 300 |

Example 20

Injectable solution

2-Diethylaminoethyl farnesylacetate hydrochloride (5 g) and 10 g of glucose were dissolved in distilled water for injection and the total amount was made 500 ml.

What is claimed is:

1. A farnesylacetic acid ester derivative selected from the group consisting of compounds represented by the general formula (I)

$$\text{structure with formula (I): farnesyl chain—CH(R}^1\text{)—C(=O)—O—A—N(R}^2\text{)(R}^3\text{)}$$

wherein

A is a straight or branched alkylene group having 2 to 10 carbon atoms in its principal chain, R' is a hydrogen atom, an alkyl group having 1 to 8 carbon atoms, a cycloalkyl group having 5 or 6 carbon atoms, an aryl group having 6 to 10 carbon atoms, an aralkyl group having 7 to 9 carbon atoms, or an alkenyl group having 2 to 15 carbon atoms, and R$^2$ and R$^3$ are the same or different and each is a hydrogen atom or an alkyl group having 1 to 8 carbon atoms, provided that the total number of carbon atoms contained in said A, R$^1$, R$^2$ and R$^3$ groups is at least five; and pharmaceutically acceptable salts thereof.

2. A farnesylacetic acid ester derivative as claimed in claim 1, which is in the form of a hydrochloride.

3. A farnesylacetic acid ester derivative as claimed in claim 1, which is in the form of a quaternary ammonium salt.

4. A farnesylacetic acid ester derivative as claimed in claim 1, wherein, in formula (I), the total number of carbon atoms contained in A, R$^1$, R$^2$ and R$^3$ is 5 to 30.

5. A farnesylacetic acid ester derivative as claimed in claim 1, wherein, in formula (I), A is an alkylene group represented by the formula $$-\underset{R^5}{\underset{|}{\overset{R^4}{\overset{|}{C}}}}-\underset{R^7}{\underset{|}{\overset{R^6}{\overset{|}{C}}}}-(CH_2)_n-$$

wherein R$^4$, R$^5$, R$^6$ and R$^7$ are the same or different and each is a hydrogen atom or a lower alkyl group having 1 to 5 carbon atoms and n is an integer of 0 or 1.

6. A farnesylacetic acid ester derivative as claimed in claim 1, which, when in the free form, is represented by the formula (I-1)

$$\text{structure (I-1): farnesyl chain—CH(R}^{1a}\text{)—C(=O)—O—A'—N(R}^{2a}\text{)(R}^{3a}\text{)}$$

wherein

A' is a lower alkylene group represented by —CH$_2$CH$_2$— —CH$_2$CH$_2$CH$_2$—, —CH(CH$_3$)—CH$_2$—, —CH$_2$—CH(CH$_3$)—, —C(CH$_3$)$_2$—CH$_2$—, —CH$_2$—C(CH$_3$)$_2$— or —C(CH$_3$)$_2$—CH$_2$CH$_2$—, R$^{1a}$ is a hydrogen atom, a lower alkyl group having 1 to 5 carbon atoms, an alkenyl group having 3 to 10 carbon atoms, cyclohexyl, phenyl or benzyl, and R$^{2a}$ and R$^{3a}$ are the same or different and each is a hydrogen atom or, a lower alkyl group having 1 to 5 carbon atoms, provided that the total number of carbon atoms contained in A', R$^{1a}$, R$^{2a}$ and R$^{3a}$ is 5 to 30.

7. A farnesylacetic acid ester derivative as claimed in claim 6, wherein, in formula (I-1), $R^{1a}$ is a hydrogen atom.

8. A farnesylacetic acid ester derivative as claimed in claim 7, wherein, in formula (I-1), $R^{2a}$ and $R^{3a}$ are each methyl.

9. A farnesylacetic acid ester derivative as claimed in claim 7, wherein, in formula (I-1), $R^{2a}$ and $R^{3a}$ are each ethyl.

10. A farnesylacetic acid ester derivative as claimed in claim 6, wherein, in formula (I-1), $R^{1a}$ is a lower alkyl having 1 to 5 carbon atoms, an alkenyl group having 3 to 10 carbon atoms, cyclohexyl, phenyl or benzyl.

11. The farnesylacetate acid derivative according to claim 8, which is 3-dimethylaminopropyl farnesylacetate.

12. The farnesylacetate acid ester derivative according to claim 8 which is 1,1-dimethyl-2-dimethylaminoethyl farnesylacetate.

13. The farnesylacetate acid ester derivative according to claim 9 which is 2-diethylaminoethyl farnesylacetate.

14. The farnesylacetate acid ester derivative according to claim 9 which is is 2-farnesylacetoxyethyltriethylammonium bromide.

15. The farnesylacetate acid ester derivative according to claim 10 which is 2-dimethylaminoethyl α-benzyl-farnesylacetate.

16. An antiulcer composition containing (1), as the active ingredient thereof, a farnesylacetic acid ester derivative selected from the group consisting of compounds represented by the general formula (I)

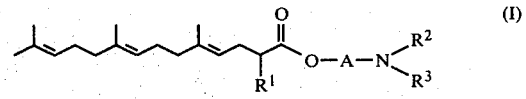

wherein
A is a straight or branched alkylene group having 2 to 10 carbon atoms in its principal chain,
R' is a hydrogen atom, an alkyl group having 1 to 8 carbon atoms, a cycloalkyl group having 5 to 6 carbon atoms, an aryl group having 6 to 10 carbon atoms, an aralkyl group having 7 to 9 carbon atoms, or an alkenyl group having 2 to 15 carbon atoms, and
$R^2$ and $R^3$ are the same or different and each is a hydrogen atom or an alkyl group having 1 to 8 carbon atoms,
provided that the total number of carbon atoms contained in said A, $R^1$, $R^2$ and $R^3$ groups is at least five; and pharmaceutically acceptable salts thereof, and (2) a pharmceutically acceptable diluent or carrier.

17. An antiulcer agent as claimed in claim 16, wherein the farnesylacetic acid ester derivative, when in the free form, is represented by the formula (I-1)

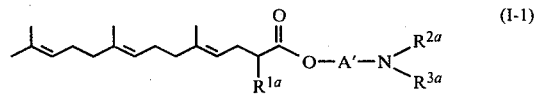

wherein,
A' is a lower alkylene group represented by —CH$_2$CH$_2$—, —CH$_2$CH$_2$CH$_2$—, —CH(CH$_3$)—CH$_2$—, —CH$_2$—CH(CH$_3$)—, —C(CH$_3$)$_2$—CH$_2$—, —CH$_2$—C(CH$_3$)$_2$— or —C(CH$_3$)$_2$—CH$_2$CH$_2$—,
$R^{1a}$ is a hydrogen atom, a lower alkyl group having 1 to 5 carbon atoms, an alkenyl group having 3 to 10 carbon atoms, cyclohexyl, phenyl or benzyl, and
$R^{2a}$ and $R^{3a}$ are the same or different and each is a hydrogen atom or, a lower alkyl group having 1 to 5 carbon atoms, provided that the total number of carbon atoms contained in A', $R^{1a}$, $R^{2a}$ and $R^{3a}$ is 5 to 30.

18. A method of treating ulcers of the mammalian digestive tract in an afflicted host which comprises administering to said host a farnesylacetic acid ester derivative or a pharmaceutically acceptable salt thereof as defined in claim 1 in a pharmaceutically acceptable carrier in dosage unit form in a daily dose ranging from about 100 mg to about 2500 mg of said derivative or pharmaceutically acceptable salt thereof.

19. A method as defined in claim 18 wherein administration is oral.

20. A method as defined in claim 18 wherein administration is parenteral.

* * * * *